United States Patent
Chirivi et al.

(10) Patent No.: US 11,066,462 B2
(45) Date of Patent: Jul. 20, 2021

(54) METHOD FOR THE TREATMENT OF IDIOPATHIC PULMONARY FIBROSIS

(71) Applicant: Citryll B.V., Oss (NL)

(72) Inventors: Renato Gerardus Silvano Chirivi, Oosterhout (NL); Jozef Maria Hendrik Raats, Nijmegen (NL)

(73) Assignee: Citryll B.V., Oss (NL)

( * ) Notice: Subject to any disclaimer, the term of this patent is extended or adjusted under 35 U.S.C. 154(b) by 30 days.

(21) Appl. No.: 15/534,699

(22) PCT Filed: Dec. 11, 2015

(86) PCT No.: PCT/EP2015/079443
§ 371 (c)(1),
(2) Date: Jun. 9, 2017

(87) PCT Pub. No.: WO2016/092082
PCT Pub. Date: Jun. 16, 2016

(65) Prior Publication Data
US 2017/0334978 A1    Nov. 23, 2017

(30) Foreign Application Priority Data
Dec. 11, 2014   (EP) .................................... 14197374

(51) Int. Cl.
*A61K 39/00*    (2006.01)
*C07K 16/18*    (2006.01)
*C07K 16/44*    (2006.01)

(52) U.S. Cl.
CPC .......... *C07K 16/18* (2013.01); *A61K 39/0005* (2013.01); *C07K 16/44* (2013.01); *A61K 2039/505* (2013.01); *A61K 2039/54* (2013.01); *A61K 2039/575* (2013.01); *C07K 2317/34* (2013.01); *C07K 2317/565* (2013.01)

(58) Field of Classification Search
CPC .... C07K 16/18; C07K 16/44; C07K 2317/34; C07K 2317/565; A61K 2039/505; A61K 2039/54; A61K 2039/575; A61K 39/0005
See application file for complete search history.

(56) References Cited

U.S. PATENT DOCUMENTS

| | | | |
|---|---|---|---|
| 9,109,019 | B2 | 8/2015 | Raats |
| 9,422,358 | B2 | 8/2016 | Leenders et al. |
| 2011/0243945 | A1 | 10/2011 | Raats et al. |
| 2015/0307603 | A1 | 10/2015 | Raats et al. |
| 2016/0311900 | A1 | 10/2016 | Leenders et al. |

FOREIGN PATENT DOCUMENTS

| | | |
|---|---|---|
| JP | 2014517296 A | 7/2014 |
| WO | 2009147201 A2 | 12/2009 |
| WO | 2011070172 A1 | 6/2011 |
| WO | 2013144758 A1 | 10/2013 |

OTHER PUBLICATIONS

Edwards et al. J. Mol. Biol., 334:103-118. (Year: 2003).*
Fischer A et al. Lung disease with anti-CCP antibodies but not rheumatoid arthritis or connective tissue disease. Respiratory Medicine, 106:1040-1047. (Year: 2012).*
Lloyd et al. Protein Eng. Design & Select, 22(3): 159-168. (Year: 2009).*
Obayashi Y et al. The role of neutrophils in the pathogenesis of idiopathic pulmonary fibrosis. Chest, 1997, 112(5): 1338-1343. (Year: 1997).*
Interstitial lung disease and Pulmonary Fibrosis, description sheet from Columbia University, from columbiasurgery.org/conditions-and-treatments/interstitial-lung-disease-and-pulmonary-fibrosis. Retrieved from internet Mar. 2, 2020. (Year: 2020).*
Cavagna et al, The Multifaceted Aspects of Interstitial Lung Disease in Rheumatoid Arthritis.., Jan. 1, 2013, Biomed Research International, vol. 17, No. 2, pp. 270-13.
Giles et al, Association of Cross-Reactive Antibodies Targeting Peptidyl-Arginine Deiminase 3 and 4 with Rheumatoid Arthritis-Associated Interstitial, Jun. 5, 2014, Lung Disease, PLOS ONE, vol. 9 No. 6, pp. 1-8.
PCT International Search Report, PCT/EP2015/079443, dated Mar. 4, 2016.
PCT International Search Report and Written Opinion, PCT/EP2015/079443, dated Mar. 4, 2016.
PCT International Preliminary Report on Patentability, PCT/EP2015/079443, dated Jun. 22, 2017.
Solomon, Joshua J, et al. "IgA Antibodies Directed Against Citrullinated Protein Antigens are Elevated in Patients With Idiopathic Pulmonary Fibrosis." Chest, vol. 157, No. 6, 2019, pp. 1513-1521.
Matson S, Solomon, et al. "Anti-CCP3.1 and Anti-CCP3-IgA are Elevated in RA-Free Subjects with Idiopathic Pulmonary Fibrosis" [abstract]. Arthritis Rheumatol. 2016; 68 (suppl 10). https://acrabstracts.org/abstract/anti-ccp3-1-and-anti-ccp3-iga-are-elevated-in-ra-free-subjects-with-idiopathic-pulmonary-fibrosis/.
Ishigami, Akihito, Prospects for Geriatrics, Citrullinated Molecules and Geriatric Disease, The Japanese Journal of Geriatrics, Jul. 2014, vol. 51, No. 4 (314-320). Translated from Google Translation, total pp. 15.
JP Office Action—Notice of Reasons for Refusal (with Translation), Application No. 2017-549593, dated Dec. 17, 2019, 11 pages.

* cited by examiner

*Primary Examiner* — Kimberly Ballard
(74) *Attorney, Agent, or Firm* — Patent Law Works, LLP

(57) ABSTRACT

The invention is in the field of methods and preparations for medical treatments, in particular the treatment of idiopathic pulmonary fibrosis (IPF). The invention provides such methods wherein antibodies or fragments thereof that react with selected citrullinated epitopes are used in the treatment of IPF. Antibodies against citrullinated epitopes situated at the amino terminus of histone polypeptides H2A and H4 were found to be particularly useful. The invention therefore relates to an antibody specifically reactive with a citrullinated epitope on the N-terminus of deiminated histone H2A or H4 for use in the prevention or treatment of idiopathic pulmonary fibrosis.

7 Claims, 8 Drawing Sheets

Figure 1:
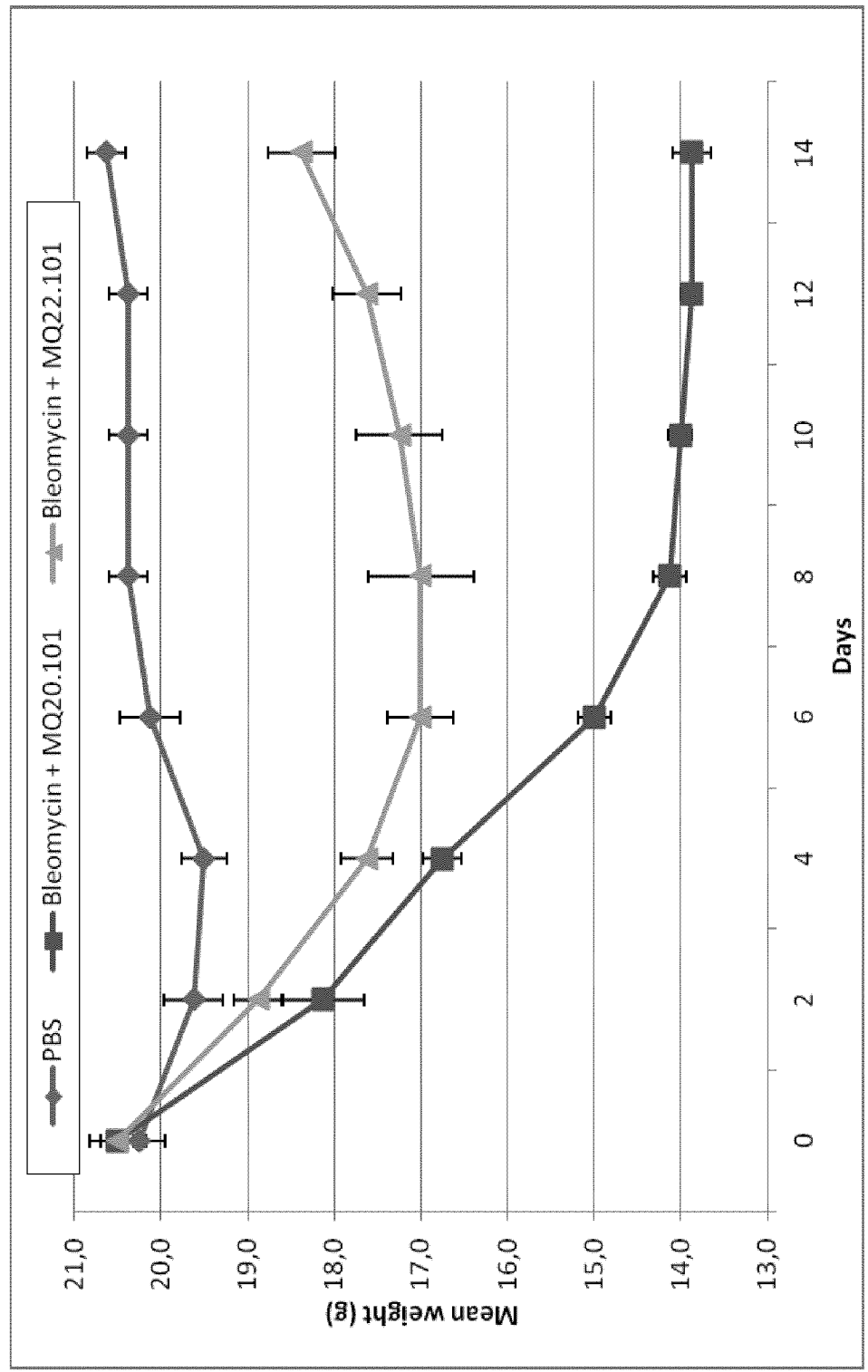

Specification includes a Sequence Listing.

METHOD FOR THE TREATMENT OF IDIOPATHIC PULMONARY FIBROSIS

CROSS-REFERENCE TO RELATED APPLICATIONS

This application is a national phase entry under 35 U.S.C. § 371 of International Patent Application PCT/EP2015/079443, filed Dec. 11, 2015, designating the United States of America and published in English as International Patent Publication WO 2016/092082 A1 on Jun. 16, 2016, which claims the benefit under Article 8 of the Patent Cooperation Treaty to European Patent Application Serial No. 14197374.3, filed Dec. 11, 2014.

FIELD OF THE INVENTION

The invention is in the field of methods and preparations for medical treatments, in particular the treatment of idiopathic pulmonary fibrosis (IPF). The invention provides such methods wherein antibodies or fragments thereof that react with selected citrullinated epitopes are used in the treatment of IPF. Antibodies against citrullinated epitopes situated at the amino terminus of histone polypeptides H2A and H4 were found to be particularly useful.

BACKGROUND OF THE INVENTION

Idiopathic pulmonary fibrosis (IPF) is a complex chronic fibroproliferative lung disease of unknown etiology, with an increasing incidence. The disease is characterized by progressive accumulation of extracellular matrix within the interstitium. It is a progressive and irreversible disease with an estimated median survival of only 36 months. Historically, corticosteroids (e.g. prednisolone) in combination with immunosuppressives (e.g. azathioprine) and/or N-acetylcysteine, have been advocated as reasonable, but unproven treatment strategy for IPF. Another drug which has been approved for the treatment of IPF in Japan, Europe, India and Canada is Pirfenidone. Pirfenidone is an orally administered pyridine that has combined anti-inflammatory, anti-oxidant and anti-fibrotic actions in experimental models of pulmonary fibrosis, although the precise mechanism of action is unknown. It is the only drug for which an improved progression-free survival time has been observed. At present, there is no scientific evidence to suggest that current therapeutic strategies can reverse fibrosis in IPF; the realistic goal of therapies under investigation is to stabilize or reduce the rate of disease progression.

It is clear that better and more effective treatments for IPF are urgently needed.

SUMMARY OF THE INVENTION

We provide evidence herein that the symptoms of IPF may be prevented, ameliorated or abolished when an antibody directed against a citrullinated epitope on a peptide derived from the N-terminus of deiminated histone H2A or H4 is administered to a subject in need of such a treatment. The same effect may be achieved by immunization with an N-terminal peptide derived from deiminated histone H2A or H4 comprising a citrulline residue.

DETAILED DESCRIPTION OF THE INVENTION

In the experiments that lead to the present invention, we employed an accepted mouse model for IPF. In that model, fibrosis in lungs of C57BL/6 mice was induced by oropharyngeal instillation of bleomycin as detailed in example 1. Control animals received an oropharyngeal instillation of PBS.

Antibodies specifically reactive with a citrullinated epitope on the N-terminus of deiminated histone H2A or H4 were administered to bleomycin-treated animals and shown to be effective in treating the symptoms of IPF. Such antibodies are herein after termed Anti-Citrulline Protein Antibodies, abbreviated as ACPA.

ACPA may be obtained in a number of different ways, known per se to the skilled person. For example, ACPA may be generated by immunizing an experimental animal with an appropriate antigen, such as a peptide comprising a citrullinated epitope on the N-terminus of deiminated histone H2A or H4. Representative examples of such peptides may comprise the following amino acid sequences: SGCitGKQGGKARA (SEQ ID NO: 1) and SGCitGKGGKGLGKGGAKRHRKVLR (SEQ ID NO: 2), Table 1.

Antibodies thus obtained may be tested for their specificity of binding to the citrullinated epitope on the N-terminus of histone H2A or H4. This may advantageously be done by comparing the binding of the antibody to a peptide according to SEQ ID NO: 1 or SEQ ID NO: 2 with the binding to a control peptide that does not carry the citrullinated epitope on the N-terminus of histone H2A or H4. Representative examples of a peptide which does not contain the citrullinated epitope on the N-terminus of histone H2A or H4 are for instance peptides comprising the amino acid sequence SGRGKQGGKARA (SEQ ID NO: 3) and SGRGKGGKGLGKGGAKRHRKVLR (SEQ ID NO: 4), Table 1.

TABLE 1

| Peptides | |
|---|---|
| SEQ ID NO: | Amino-acid sequence |
| SEQ ID NO: 1 | SGCitGKQGGKARA |
| SEQ ID NO: 2 | SGCitGKGGKGLGKGGAKRHRKVLR |
| SEQ ID NO: 3 | SGRGKQGGKARA |
| SEQ ID NO: 4 | SGRGKGGKGLGKGGAKRHRKVLR |

The binding of an antibody to a citrullinated epitope on the N-terminus of deiminated histone H2A or H4 is considered to be specific if the antibody binds to a citrullined epitope on the N-terminus of deiminated histone H2A or H4 whereas it binds with less affinity to the control peptide not comprising the citrullinated epitope on the N-terminus of histone H2A or H4. Less affinity in this context means a binding of at least 50% less, such as 75%, 90%, 95% or more than 95% less. More preferably, the binding of the antibody to the citrullinated epitope on the N-terminus of deiminated histone H2A or H4 is easily detectable whereas the binding of the antibody to a peptide with the same amino acid sequence wherein the citrulline residue is replaced by an arginine residue is not detectable.

The specifically reactive antibodies disclosed herein (RhmAb2.102, RhmAb2.108, RhmAb2.109, RhmAb2.110, RhmAb2.111 RhmAb2.112, MQ22.101, MQ22.102 and MQ22.101b/d) were all found to react with peptides according to SEQ ID NO: 1 or SEQ ID NO: 2 wherein they were negative for binding to peptides with SEQ ID NO: 3 or SEQ ID NO: 4. These antibodies have also been previously disclosed in WO2011/070172 and in WO2009/147201.

Mouse monoclonal antibody Rmmab22.101 (abbreviated herein as MQ22.101) was chosen as a model antibody, representing the class of antibodies that specifically bind to a citrullinated epitope on the N-terminus of deiminated histone H2A or H4.

The therapeutic activity of the MQ22.101 antibody was established as follows. Bleomycin treated mice received intraperitoneal injections containing 1 mg of monoclonal antibody MQ22.101 or 1 mg of an isotype matched control antibody MQ20.101 obtained from ModiQuest Research B.V. (Cat no, MQ20.101).

Monoclonal antibodies were administered to the animals on days 0, 2 and 5. Weight of all animals was assessed each other day starting from day 0 until day 14. Weight loss of the animals was taken as a measure for the severity of the disease.

We observed that mice treated with Bleomycin+MQ20.101 lost weight gradually over time with 32% of weight loss on day 14 compared to PBS treated control animals which did not lose any weight (FIG. 1). In the MQ22.101 treated group we found that animals where protected against massive weight loss with a maximum of 17% on day 6, after which animals gradually gained weight over time (10% weight loss on day 14 compared to day 0).

Figure 2:
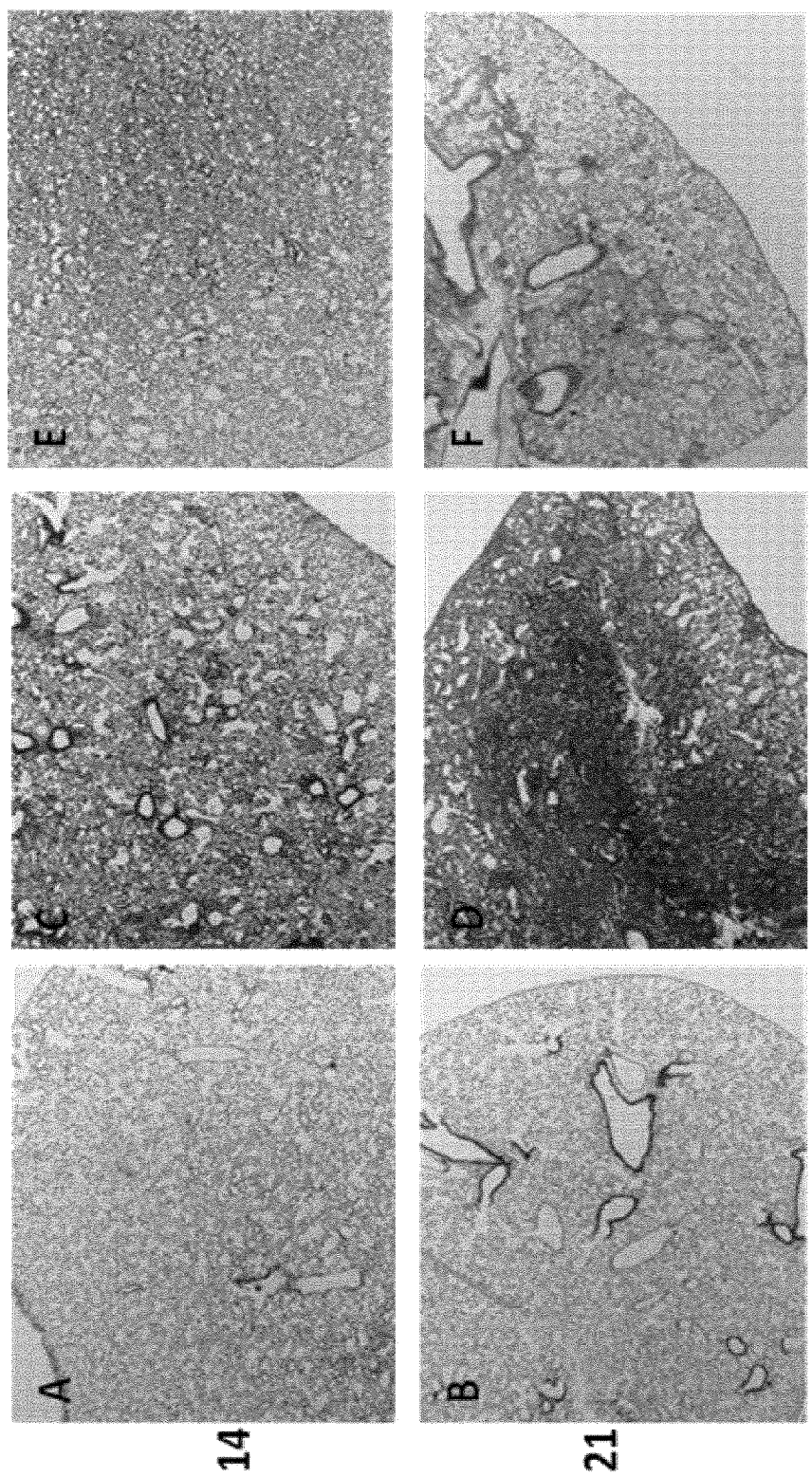

Two or 3 weeks after bleomycin or PBS instillation, mice were killed by cervical dislocation under isoflurane anesthesia, and lungs and bronchoalveolar lavage (BAL) fluids were collected. Lungs were fixed, paraffin embedded, and the sections were Masson stained in order to assess the amount of inflammation/fibrosis (FIG. 2).

We observed that bleomycin+MQ20.101 treated mice had massive amounts of fibrotic tissue present in the lungs as compared to lungs from control mice (PBS treated) which did not have any signs of fibrosis. MQ22.101 was able to protect the bleomycin treated mice from inflammatory responses in the lung and thus the formation of fibrosis (FIG. 2).

Figure 3A:
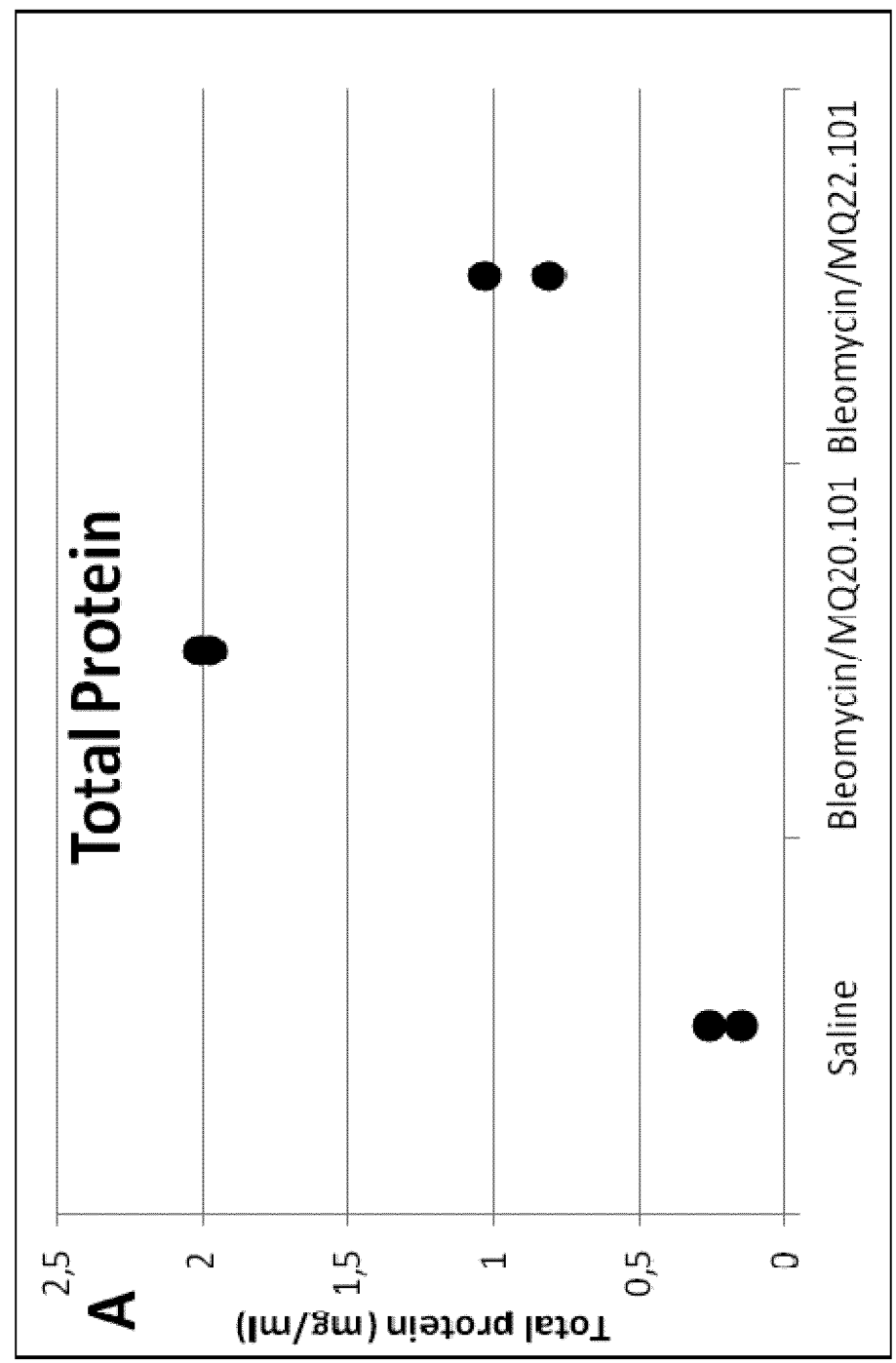
Figure 3B:
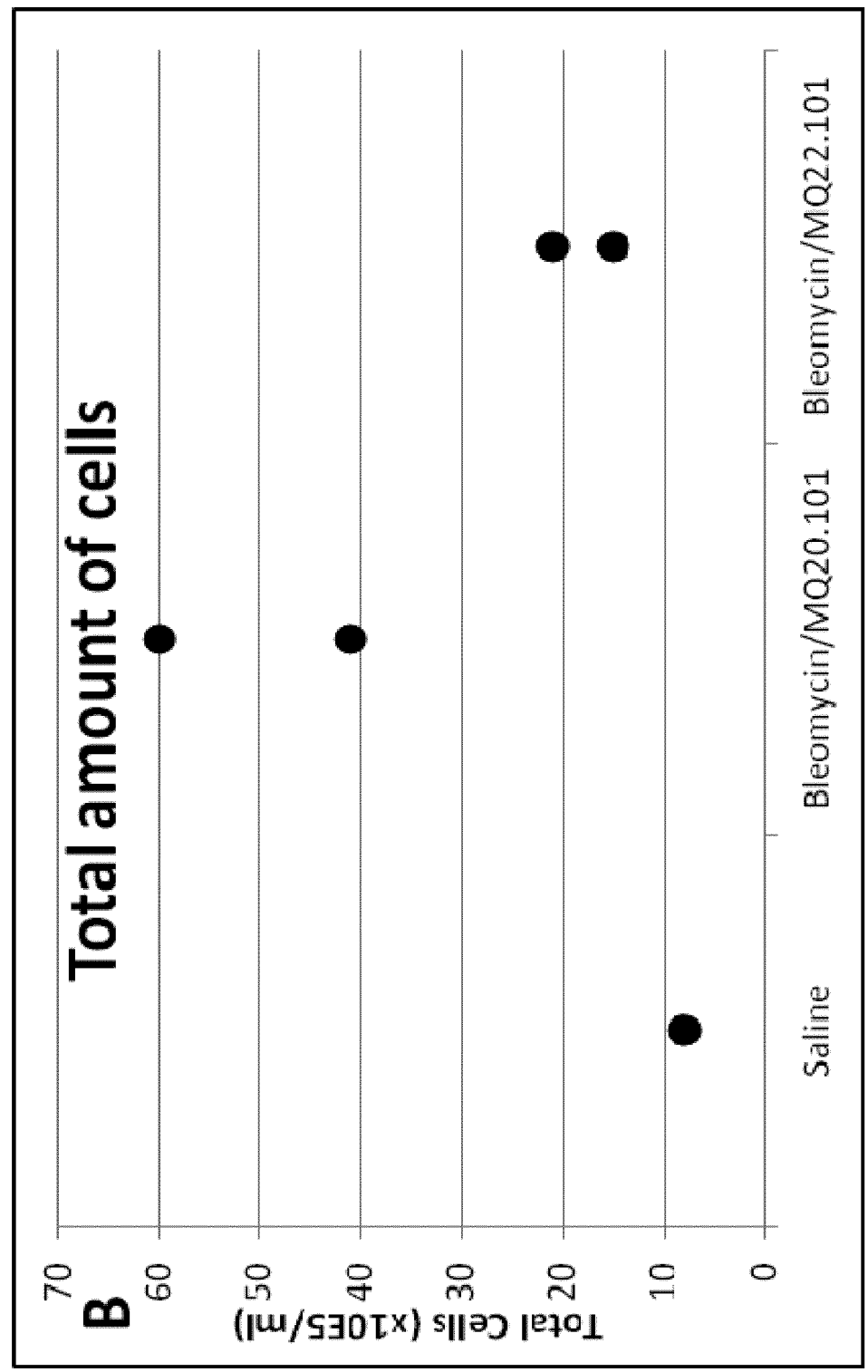
Figure 3C:
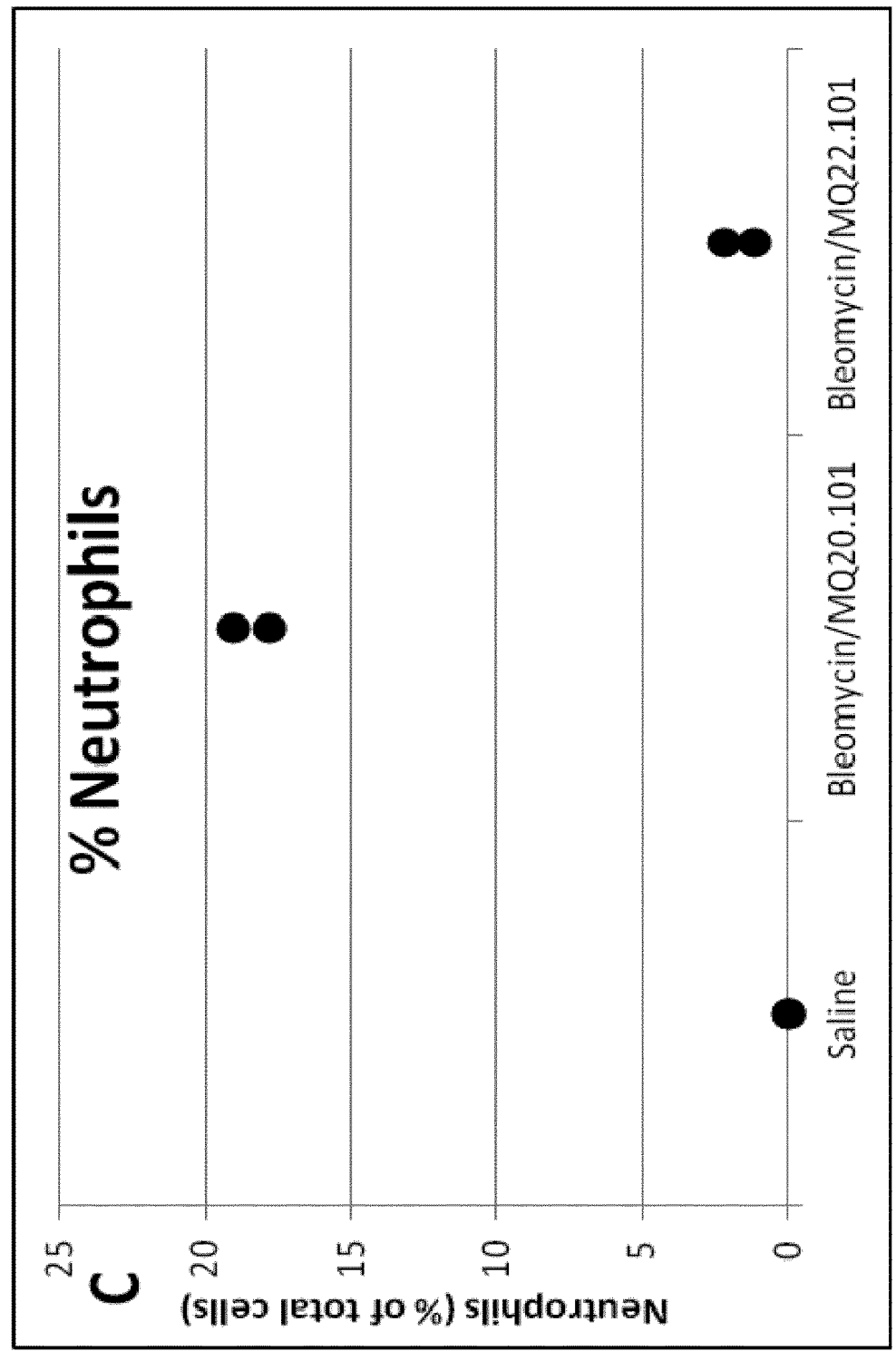
Figure 3D:
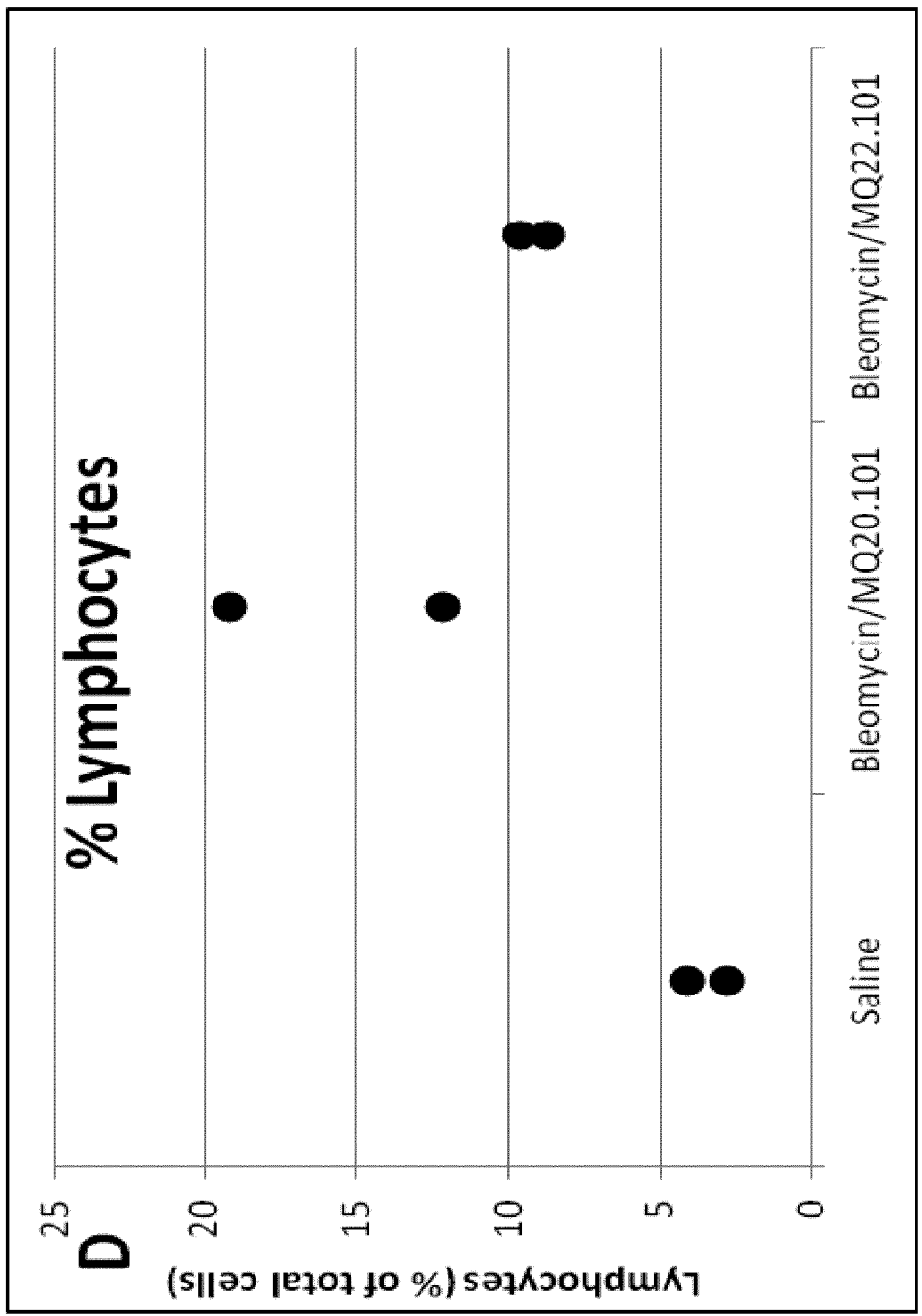
Figure 3E:
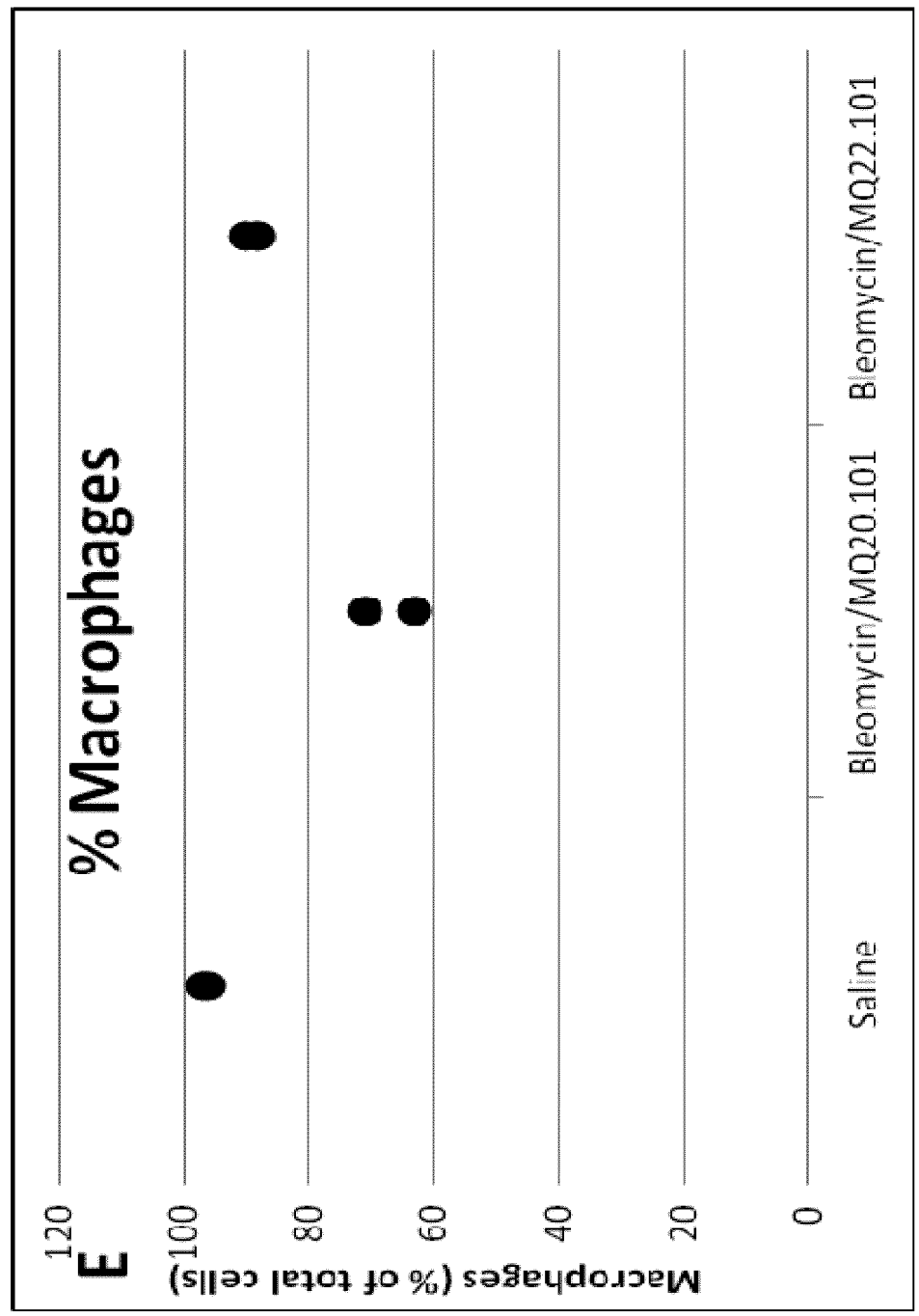

Total protein in BAL is a measure for lung injury. BAL fluid from bleomycin+MQ20.101 treated mice contained respectively 4 and 2 times more protein compared to saline treated and MQ22.101 treated mice (FIG. 3A). In addition, total and differential cell counts (Neutrophils, macrophages and lymphocytes) were measured in BAL fluid. Total amount of cells was markedly increased in bleomycin+MQ20.101 treated mice if compared to saline treated and MQ22.101 treated mice (FIG. 3B). When looking at differential cell counts (FIGS. 3C-E), the most striking difference was found with neutrophils; BAL from bleomycin+MQ20.101 treated mice contained 20% neutrophils, whereas the percentage of neutrophils in BAL from saline treated and MQ22.101 treated mice was close to 0% (FIG. 3C).

The above described experiment was repeated with a humanized version of MQ22.101, with some minor modifications as described in example 2. The making of the humanized version of MQ22.101, MQ22.101b/d, is described in example 7. Variable heavy (VH) and variable light (VL) chain fragments from MQ22.101 were cloned into a human IgG1 kappa backbone. VH and VL domains were subsequently humanized by CDR grafting. Table 2 shows the VH CDR1, -2 and -3 polypeptides (SEQ ID NO: 5, 6 and 7) and VL CDR1, -2 and -3 polypeptides (SEQ ID NO: 8, 9 and 10) according to IMGT (world wide web at imgt.org).

Figure 4:
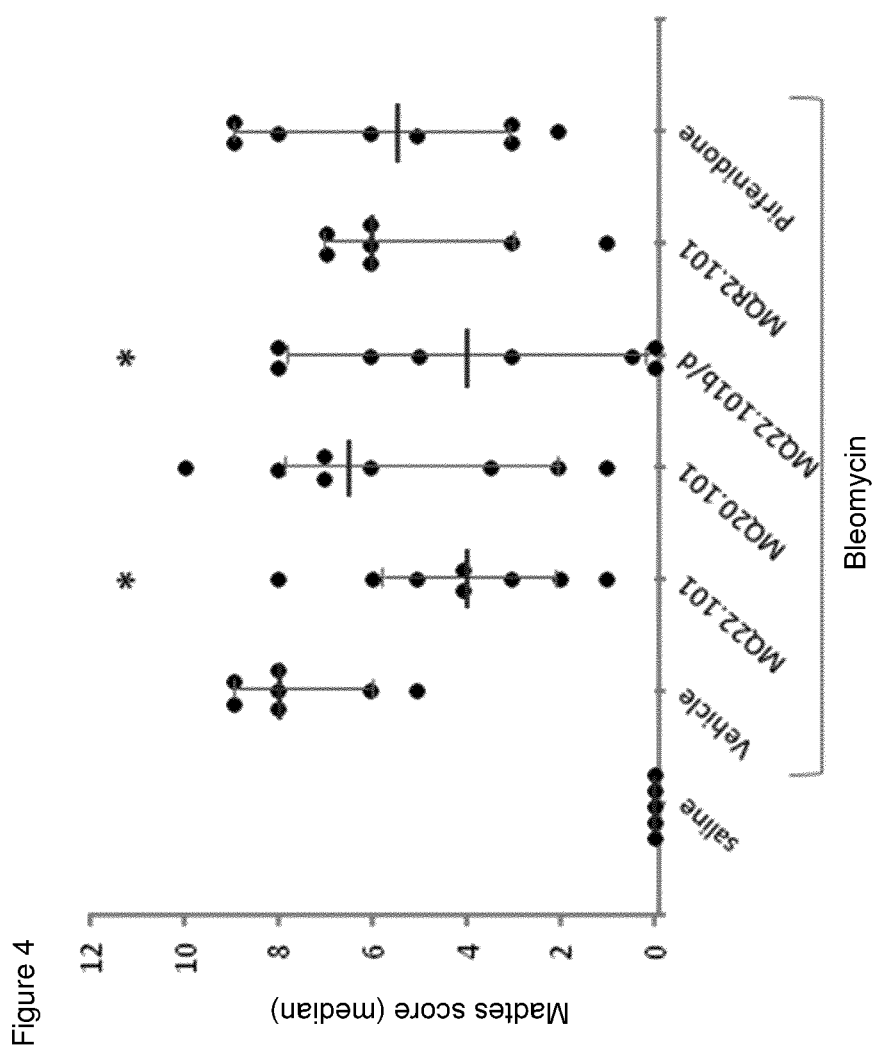

In the experiment described in example 2, histopathological analysis of inflammation and fibrosis in the lung was assessed using Madtes scoring (Madtes D K et al., A J Respir Cell Mol Biol 20, 924-934, 1999). Only antibodies MQ22.101 and its humanized counterpart MQ22.101b/d diminished inflammation and fibrosis in the lung if compared to control antibodies MQ20.101 and MQR2.101 (FIG. 4). MQR2.101 obtained from ModiQuest Research B.V. (Cat no, MQ20.101), is the isotype matched control antibody for MQ22.101b/d.

TABLE 2

VH and VL CDR sequences derived from MQ22.101b/d*

| SEQ ID NO: | VH or VL | CDR | Amino-acid sequence |
|---|---|---|---|
| SEQ ID NO: 5 | VH | CDR1 | GYTFTNY |
| SEQ ID NO: 6 | VH | CDR2 | INTYSGEA |
| SEQ ID NO: 7 | VH | CDR3 | LRGYTYQSFDEGGDY |
| SEQ ID NO: 8 | VL | CDR1 | QSLLDSDGKTY |
| SEQ ID NO: 9 | VL | CDR2 | LVS |
| SEQ ID NO: 10 | VL | CDR3 | WQGTHFPYT |

*CDR annotation according to IMGT database.

It was concluded that ACPAs and in particular MQ22.101 and its humanized counterpart MQ22.101b/d protect mice from inflammation and fibrosis in the lung.

Since the model system chosen here is representative for the human version of IPF, it is concluded that an antibody specifically reactive with a citrullinated epitope on the N-terminus of deiminated histone H2A or H4 may be used in the prevention or treatment of idiopathic pulmonary fibrosis.

Next from the use in passive therapeutic vaccination (administering of antibodies) as described above, the invention may also be practiced by inducing an immune response in vivo in a subject in need thereof. For that purpose, we employed peptides comprising a citrullinated epitope on the N-terminus of deiminated histone H2A or H4. Such peptides were administered subcutaneously (active therapeutic vaccination) in a mouse and elicited the same titers of specific ACPAs in mice as the titers found in mice that were passively immunized. Such mice were no longer responsive to bleomycine installation and showed the same lack of symptoms as their passively immunized counterparts.

The term: "specifically reacts with citrulline" or "reactive with a citrullinated epitope" or "specifically reactive with a citrulline epitope" in this context refers to an antibody or antibody fragment that reacts with a structure such as a peptide containing a citrulline residue whereas the antibody or antibody fragment reacts less or preferably not at all with the same structure containing an arginine residue instead of the citrulline residue. The term peptide should be interpreted as a structure that is capable of presenting the citrulline residue in the correct context for immunoreactivity with the antibodies as described herein, preferably in the same context as it appears in the human or animal body, preferably in the context of a native polypeptide. Native antibodies (also known as immunoglobulins) are gamma globulin proteins that may be found in blood or other bodily fluids of vertebrates, and are used by the immune system to identify and neutralize foreign objects, such as bacteria and viruses.

Native antibodies are typically made of basic structural units—each with two large heavy chains and two small light chains—to form, for example, monomers with one unit, dimers with two units or pentamers with five units. Antibodies are produced by a white blood cell called a B cell. There are several different types of heavy chains, resulting in different kinds of antibodies. Antibodies may be grouped into different isotypes based on which heavy chain they possess. Five different antibody isotypes are known in mammals which perform different roles, and help direct the appropriate immune response for each different type of foreign object they encounter. Some animal species such as Camelids (e.g. llamas) and sharks may have aberrant antibody structures.

Although the general structure of all antibodies is very similar, a small region at the tip of the protein is extremely variable, allowing millions of antibodies with slightly different tip structures to exist. This region is known as the hypervariable region. Each of these variants can bind to a different target, known as an antigen. This huge diversity of antibodies allows the immune system to recognize an equally wide diversity of antigens.

The unique part of the antigen recognized by an antibody is called an epitope. These epitopes bind with their antibody in a highly specific interaction that allows antibodies to identify and bind only their unique antigen in the midst of the millions of different molecules that make up an organism. Recognition of an antigen by an antibody tags it for attack by other parts of the immune system. Antibodies can also neutralize targets directly, for example, by binding to a part of a pathogen that it needs to cause an infection.

The large and diverse population of antibodies is generated by random combinations of a set of gene segments that encode different antigen binding sites (or paratopes), followed by random mutations in this area of the antibody gene, which create further diversity. Antibody genes also re-organize in a process called class switching that changes the base of the heavy chain to another, creating a different isotype of the antibody that retains the antigen specific variable region. This allows a single antibody to be used in several different isotypes by several different parts of the immune system.

The term "antibodies" or "antibody" as used herein refers to a structure, preferably a protein or polypeptide structure, capable of specific binding to a target molecule often referred to as "antigen".

An antibody may be selected from the group consisting of single chain antibodies, single Chain Variable Fragments (scFvs), Fragment antigen binding regions (Fabs), recombinant antibodies, monoclonal antibodies, fusion proteins comprising the antigen-binding domain of a native antibody or an aptamer, single domains antibodies (sdabs), also known as VHH antibodies, nanobodies (Camelids derived single domain antibodies), shark IgNAR derived single domain antibody fragments called VNAR or fragments or a part thereof, In another preferred embodiment, an antibody is a fusion protein comprising the antigen-binding domain of a native antibody.

The term "or part thereof" or "fragments thereof" in the context of an antibody or other specific binding molecule is meant to refer to the part of the antibody or specific binding molecule that makes up the specific binding site of the antibody or specific binding molecule and may be interpreted as the part of an antibody or specific binding molecule that is still capable to react with the same epitope as the entire antibody or specific binding molecule.

Human antibodies or fragments thereof are a preferred embodiment of the invention. Preferably IgG1 antibodies having an IgG1 heavy chain and a lambda or kappa light chain may advantageously be used. However, other human antibody isotypes are also encompassed by the invention, including IgG2, IgG3, IgG4, IgM, IgA1, IgA2, IgAsec, IgD and IgE in combination with a kappa or lambda light chain. Also all animal-derived antibodies of various isotypes can be used in the invention. The antibodies can be full-size antibodies or antigen-binding fragments of antibodies, including Fab, F(ab')2, single chain Fv fragments, or single domain VHH, VH or VL single domains.

The term "antibodies reactive with a citrullinated epitope" is to be interpreted as an antibody that specifically reacts with a citrulline residue in the context of a larger structure such as a peptide or a peptide nucleic acid or a peptide mimicking structure.

Citrulline is an amino acid that is not incorporated into proteins during normal translation, however, it may be generated by post-translational modification of an arginine residue by peptidylarginine deiminase (PAD).

Citrullination is the posttranslational conversion of arginine residues to citrulline residues, which is catalyzed by peptidylarginine deiminase (PAD). Peptidylarginine deiminase (PAD; EC 3.5.3.15) enzymes catalyse the conversion of arginine residues to citrulline residues in proteins. No tRNA exists for citrulline, the presence of citrulline residues in proteins is exclusively the result of post-translational modification. In mammals (humans, mice and rats) five PAD isotypes (PAD1-PAD6; 'PAD4' and 'PAD5' are used for the same isotype), each encoded by a distinct gene, have been identified (Vossenaar et al, Bioessays 25, 1106-1118, 2003). All these enzymes rely strongly on the presence of Ca2+ for activity and are unable to convert free L-arginine into free L-citrulline. Free L-arginine can be converted to free L-citrulline by nitric oxide synthase (EC 1.14.13.39) in eukaryotes or by arginine deiminase (EC 3.5.3.6) in bacteria. These enzymes are not Ca2+ dependent.

The most pronounced difference between the highly homologous PAD enzymes is their tissue-specific expression. In epidermis PAD1 (synonyms: PAD I, PAD type I) is involved in the citrullination of keratin filaments during the final stages of keratinocyte differentiation, which is important for the reorganization of the cornified envelope. Another site of citrullination in the epidermis is the hair follicle, which contains PAD3 (synonyms PAD III, PAD type III) and its natural substrate trichohyalin (THH). THH is a major structural protein of the inner root sheath cells and the medulla layer of the hair follicle and, to a lesser extent, of other specialized epithelia. The most recently identified PAD isotype, PAD6 (synonym: ePAD), was found in cytoplasmic sheets of mouse oocytes, which play an important role in early embryogenesis. The expression of its human orthologue was found to be restricted to ovary, testis and peripheral blood leukocytes (Chavanas et al., Gene 330; 19-27, 2004). Originally, this PAD isotype was designated ePAD, but based upon the systematic numbering of other PADs, this isotype was renamed PAD6 (Vossenaar et al., Bioessays 25 1106-1118, 2003). The most widely expressed isotype, PAD2 (synonyms PAD II, PAD type II, PAD-H19), is present in many different tissues, like skeletal muscle, brain, spleen, secretory glands and macrophages. Despite this broad expression pattern, only myelin basic protein (MBP) and vimentin have been identified as natural substrates. In multiple sclerosis (MS) patients develop an autoimmune response against MBP. MBP is an abundant protein of the myelin sheath, and its citrullination occurs during development of the central nervous system. Citrullination of vimentin was observed during calcium-ionophore induced apoptosis of human and mouse macrophages and, as described above, citrullinated vimentin was shown to be the target of the RA-specific anti-Sa autoantibodies. In contrast to the PADs discussed above, which are all mainly localized in the cytoplasm of cells, the PAD4 isotype (synonyms: PAD IV, PAD type IV, HL-60 PAD, PAD V, PAD type V, PAD14) is localized in the nucleus. The nuclear localization signal of PAD4 was found in the N-terminal region of the protein. PAD4 is mainly expressed in peripheral blood granulocytes and monocytes. Substrates of PAD4 in the nucleus are histone core proteins (H2A, H3 and H4) and nucleophosmin/B23, a nucleolar protein that functions in ribosome assembly, nucleocytoplasmic transport and centrosome duplication.

Antibodies competing with the monoclonal antibodies as disclosed herein may also be advantageously used in the present invention. Such competing antibodies may be selected by standard procedures. In short: a binding assay such as an ELISA may be developed wherein a peptide comprising a citrullinated epitope on the N-terminus of deiminated histone H2A or H4 is immobilized on a solid support. The monoclonal antibodies as disclosed herein may be labeled and interference with their binding to the immobilized antigens may be easily determined by routine analysis. These and other, more sophisticated methods are known to the skilled person and can routinely be performed in an ordinary laboratory setting.

In particular, assays may easily be developed using any of the antigenic peptides according to SEQ ID NO: 1 or SEQ ID NO: 2 immobilized on a solid support. Monoclonal antibodies selected from the group consisting of RhmAb2.102, RhmAb2.108, RhmAb2.109, RhmAb2.110, RhmAb2.111 RhmAb2.112,MQ22.101, MQ22.102 and MQ22.101b/d may be labeled and contacted with the immobilized antigen in the presence and the absence of a test antibody. If the test antibody interferes with the binding, i.e. lowers the signal obtained with any of the labeled antibodies, it may be concluded that the test antibody competes with binding of the labeled antibody. Such a competing antibody would then be suitable for use in the methods of the invention, provided that it does not react with a peptide with the same sequence wherein the citrulline residue is replaced by an arginine residue.

Antibodies for use according to the invention may be generated essentially in two ways. First, they may be derived from the antibodies and its sequences as presented herein. Reactivity of the antibodies may even be improved by side-directed mutagenesis, chain shuffling, sexual PCR, or by other means for antibody derivation and optimisation known to the person skilled in the art. Alternatively, antibodies may be obtained by panning with any of the specifically reactive epitopes as described herein, in particular deiminated Histon 2A, a peptide comprising a sequence according to SEQ ID NO: 1 or SEQ ID NO: 2 and other particularly reactive peptides.

A person skilled in the art may use the sequences described herein to clone or generate cDNA or genomic sequences for instance such as described in the below examples. Cloning of these sequences in an appropriate eukaryotic expression vector, like pcDNA3 (In Vitrogen), or derivates thereof, and subsequent transfection of mammalian cells (like CHO cells) with combinations of the appropriate light chain and heavy chain containing vectors will result in the expression and secretion of the required antibodies Mouse monoclonal MQ22.101 may be directly expressed and secreted by their respective hybridoma cell lines as deposited. (DSMZ number ACC 3031).

The skilled person may also make analogues of the specific binding molecules as described herein by using the specific binding domains of the antibody sequences and express them in a different context such as a polypeptide such as a fusion protein. This is well known in the art.

In this document and in its claims, the verb "to comprise" and its conjugations is used in its non-limiting sense to mean that items following the word are included, but items not specifically mentioned are not excluded. In addition, reference to an element by the indefinite article "a" or "an" does not exclude the possibility that more than one of the element is present, unless the context clearly requires that there be one and only one of the elements. The indefinite article "a" or "an" thus usually means "at least one".

Without wanting to be bound by theory, we hypothesize that MQ22.101 and its human counterpart target deiminated histones in Neutrophil Extracellular Traps (NETs) and are thereby able to block the inflammatory process by inhibiting the activation and therefore the influx of inflammatory neutrophils. It has been shown by Chrysanthopoulou et al. (J Pathol 233, 294-307, 2014) that NETs are not only involved in inflammation but also in the ensuing fibrosis through their effect on fibroblast differentiation, therefore becoming an attractive target for antibody therapy according to the present invention. Antibody therapy according to the present invention does not have serious adverse effects since it does not interfere with the immune system or other general house holding pathways.

EXAMPLES

Example 1

Experimental Animal Model for Fibrosis

Female C57BL/6 mice (6-8 weeks old) were purchased from The Jackson Laboratory. All mice were maintained under pathogen-free conditions and were provided food and water ad libitum. Lung injury was induced on day 0 when the mice were 8-10 weeks old (weighing 19-21 g), by oropharyngeal instillation of bleomycin (0.045 units/mouse). Control animals received an intratracheal instillation of PBS. On days 0, 2 and 5, bleomycin treated groups received an intraperitoneal injection containing 1 mg MQ22.101 or 1 mg of control antibody MQ20.101 (irrelevant isotype matched control antibody). Weight of all animals has been assessed each other day starting from day 0 until day 14 (FIG. 1).

Two and 3 weeks after bleomycin or PBS instillation, mice were killed by cervical dislocation under isoflurane anesthesia, and lungs and bronchoalveolar lavage (BAL) fluids were collected. Lungs were fixed, paraffin embedded, and sections Masson stained in order to assess the amount of inflammation/fibrosis (FIG. 2). Protein content as well as total and differential cell counts (Neutrophils, macrophages and lymphocytes) have been measured in BAL. Protein content have been measured and total and differential cell counts have been assessed by performing cytospin with BAL fluid, staining the cells, and count and identify the different cell types based on their morphology (FIG. 3).

Example 2

Confirmation Experiments

The results obtained in example 1 were confirmed in a separate and independent experiment with a slightly altered experimental set-up.

Male C57BL/6N mice (19-21 grams at arrival) were purchased from Charles River. All mice were maintained under pathogen-free conditions and were provided food and water ad libitum. Lung injury was induced on day 0 when the mice were 8-10 weeks old (weighing 19-21 g), by intranasal challenge of bleomycin. Bleomycin sulphate has been dissolved in 0.9% solution of NaCl (10 mg/25 ml) in order to reach concentration of 0.4 mg/mL of bleomycin, and then divided into aliquots of 1 ml, stored at −20° C. The dose of bleomycin solution for challenge is 50 µl/mouse. Control animals received an intranasal challenge of PBS. Pirfenidone has been used as established treatment for pulmonary fibrosis in the bleomycin induced pulmonary fibrosis animal model. Every morning, pirfenidone for daily dosing has been prepared by solving the proper amount of pirfenidone in a 0.5% Carboxymethylcellulose Sodium Salt. Volume of administration is 10 mL/kg body weight. Pirfenidone has been administered p.o. twice daily, with 7.5 h interval between two administrations. Over the weekend, mice received the total daily dose in the morning.

Treatment: On days 0, 2 and 5 bleomycin treated groups received an intraperitoneal injection containing 1 mg mouse antibody MQ22.101, 1 mg mouse antibody "MQ20.101" (irrelevant isotype matched control antibody) or PBS. Two additional bleomycin treated groups received 1 mg humanized MQ22.101 ("MQ22.101b/d) or 1 mg human "MQR2.101" (human control antibody) on days 2 and 5. MQR2.101 is a control antibody. Pirfenidone has been dosed daily from day 0 to day 13. Two weeks after bleomycin or PBS instillation, mice were euthanized with an overdose of ketamine hydrochloride (Narketan) and xylazinehydrochloride (Rompun). Lungs were fixed with 10% buffered formalin for histopathalogical analysis (Madtes scoring: Tables 3 and 4).

For histopathological evaluation, whole lungs were embedded in paraffin and stained according to Mallory. Pulmonary histological changes were assessed using Madtes scoring methodology (Madtes D K et al. Am J Respir Cell Mol Biot 20: 924-934, 1999). Madtes scoring system takes into account fibrotic and inflammatory parameters (Tables 3 and 4; FIG. 4). Ten low power fields (LPF, ie. 50× magnification) were examined for inflammation according to the inflammation score scheme (see table 3), and for fibrosis according to the fibrosis score scheme (see table 4). Screening fields covered left and right pulmonary lobe: pulmo sinister (4xLPF) and pulmonis dexter (lobus cranialis 2xLPF, lobus caudalis 2xLPF, lobus medius 1xLPF and lobus accessorius 1xLPF). For each animal a final score was calculated as median from ten LPF.

TABLE 3

Inflammation scoring

| Inflammation | Score |
|---|---|
| Normal lung (no inflammation) | 0 |
| Scant inflammation <50% of whole pulmonary area | 1 |
| Scant inflammation >50% of whole pulmonary area | 2 |
| Moderate inflammation <50% of whole pulmonary area | 3 |
| Moderate inflammation >50% of whole pulmonary area | 4 |
| Prominent inflammation <50% of whole pulmonary area | 5 |
| Prominent inflammation >50% of whole pulmonary area | 6 |

TABLE 4

Fibrosis score scheme.

| Fibrosis | Score |
|---|---|
| Normal lung (no fibrosis) | 0 |
| Fine connective fibrils in <50% area affected by inflammation | 1 |
| Fine connective fibrils in >50% area affected by inflammation | 2 |
| Fine connective fibrils in 100% area affected by inflammation together with coarse bundles in <50% of the area of inflammation | 3 |
| Fine connective fibrils in 100% area affected by inflammation together with coarse bundles in >50% of the area of inflammation | 4 |

Total Madtes score = Inflammation + Fibrosis score

Example 3

Generation of ACPAs

Antibodies against a peptide comprising a citrullinated epitope on the N-terminus of deiminated histone H2A or H4 were raised by immunizing mice with a peptide according to SEQ ID NO: 1 and SEQ ID NO 2 in DBA/J1 mice as previously described in WO 2011/070172.

In brief: at day 125 after start of the immunization process serum samples were taken and analyzed for a citrullin specific antigen response. This was done by comparing the signals obtained in an ELISA with a peptide according to SEQ ID NO:1 as antigen in comparison with an ELISA with a peptide according to SEQ ID NO:3 as antigen. All mice showed a specific antigen specific serum titer at the time points tested.

In order to produce hybridoma cell-lines, spleens were dissected after the last boost, splenocytes were harvested from the spleen and fused with a mouse myeloma cell-line (NS-1) according to standard procedures. Antibody specificity in hybridoma supernatants were screened on citrulline containing antigen as well as on the non-citrullinated equivalent.

This resulted in a hybridoma clone producing MQ22.101 DSMZ Accession no ACC 3031). Subsequent sequencing of the heavy and light chains according to SEQ ID NO: 11 and SEQ ID NO: 12 respectively.

Example 4

Epitope Mapping of ACPAs 96-well ELISA plates were coated with neutravidin (0.1 µg/well) by overnight incubation at 4° C. Wells were washed 5 times with PBS-Tween20 (PBS-T) and blocked by a 1 hour incubation with PBS-T+1% Bovine serum albumin (BSA) at room temperature (RT). After 5 more washes with PBS-T, wells were incubated for 1 hour at RT with histone H2A derived citrulline and biotin containing peptides (0.3 µg/well) according to SEQ ID NO: 1 and SEQ ID NO: 2. All used peptides contained a free N-terminal NH2 group. After another 5 more washes with PBS-T, wells were incubated for 1 hour at RT with serial dilutions of MQ22.101 or MQ22.101b/d in PBS-T+1% BSA starting at a concentration of 10 µg/well. Wells were washed 5 times with PBS-T and incubated with rabbit-anti-human-HRP (1:2000) for 1 hour at RT followed by 5 washes with PBS-T and 3 wash steps with PBS. Wells were incubated 5 min with TMB substrate before stopping the reaction with 2M H2SO4. Optical density was measured by 450 nm and is a measure for the affinity of the antibodies used.

MQ22.101 and MQ22.101b/d bound to the N-terminal citrullinated peptide of Histone H2A (SEQ ID NO: 1) but not to the arginine containing peptide (SEQ ID NO: 3). Binding of MQ22.101 and MQ22.101b to the N-terminal citrullinated peptide of Histone H4 (SEQ ID NO: 2) showed similar results.

Example 5

Vaccination with Citrulline-Containing Peptides Generates a Protective Immune Response In Vivo An immune response was elicited in C57BL/6N mice (19-21 grams at arrival) against synthetic histone peptides containing citrulline residues of SEQ ID NO 1 or SEQ ID NO: 2 (table1). In between day 57 and 80 after the start of the immunization process serum samples were taken and analyzed for a citrulline containing peptide specific antigen response. Mice showing a specific antigen serum titer reactive with citrulline containing peptides according to SEQ ID NO 1 and/or SEQ ID NO: 2, but not with the arginine containing peptides according to SEQ ID NO 3 and SEQ ID NO: 4, were used to induce lung injury by oropharyngeal instillation of Bleomycin as explained in examples 1. Weight of all animals was assessed each other day starting from day 0 until day 21.

Two and 3 weeks after bleomycin or PBS instillation, mice were killed by cervical dislocation under isoflurane anesthesia, and lungs and bronchoalveolar lavage (BAL) fluids were collected. Lungs were fixed, paraffin embedded, and sections Masson stained in order to assess the amount of inflammation/fibrosis. Protein content as well as total and differential cell counts (Neutrophils, macrophages and lymphocytes) were measured in BAL. Protein content was measured and total and differential cell counts were assessed by performing cytospin with BAL fluid, staining the cells, and count and identify the different cell types based on their morphology.

The results on the clinical parameters of these mice were comparable, if not identical with the mice that were passively immunized with the ACPA antibody MQ22.101.

Example 6

Detection Assay for ACPAs

An assay that distinguishes between antibodies with therapeutic properties may be easily developed using an antigenic proteins according to SEQ ID NO: 1 or SEQ ID NO: 2 immobilized on a solid support. For example, MQ22.101 (or any other ACPA with therapeutic properties) may be labeled and contacted with the immobilized antigen in the presence and the absence of a test antibody. If the test antibody interferes with the binding, i.e. lowers the signal obtained with the labeled MQ22.101, it may be concluded that the test antibody competes with binding of the labeled MQ22.101. Such a competing antibody would then be suitable for use in the methods of the invention, provided that it does not react with a peptide with the same sequence wherein the citrulline residue is replaced by an arginine residue (SEQ ID NO: 3 and SEQ ID NO 4).

Example 7

Making of MQ22.101b/d

Variable heavy (VH) and variable light (VL) chain fragments from Hybridoma MQ22.101 have been obtained by RT-PCR and cloned into expression vectors containing the human IgG1 and human kappa constant domains. VH and VL domains have subsequently been humanized and germlined by CDR grafting. Table 2 shows the VH CDR1, -2 and -3 polypeptides (SEQ ID NO: 5, 6 and 7) and VL CDR1, -2 and -3 polypeptides (SEQ ID NO: 8, 9 and 10) from MQ22.101b/d.

LEGEND TO THE FIGURES

FIG. 1:
A Bleomycin induced lung fibrosis model was used to test the effect of MQ22.101 on weight loss. At day 0 mice received an oropharyngeal instillation of PBS (diamonds) or bleomycin (0.045 units/mouse)(triangles and squares). At day 0, 2 and 5 mice have been treated i.p. with 1 mg MQ22.101 (triangles), 1 mg control antibody MQ20.101 (squares) or PBS (diamonds). Animals have been weighed each other day starting from day 0 until day 14.

FIG. 2:
A Bleomycin induced lung fibrosis model was used to test the effect of MQ22.101 on the prevention of lung inflammation/fibrosis. Mice used in the experiments shown in FIGS. 2a and 2b received an oropharyngeal instillation of PBS at day 0, whereas mice used in the experiments shown in FIGS. 2c-f received an oropharyngeal instillation of bleomycin (0.045 units/mouse). At day 0, 2 and 5 mice from FIGS. 2c-d have been treated i.p. with 1 mg MQ22.101 and mice from FIGS. 2e-f have been treated i.p. with 1 mg control antibody MQ20.101. Mice were sacrificed after 14 (FIGS. 2a, 2c and 2e) or 21 days (FIGS. 2b, 2d and 2f), lungs fixed, paraffin embedded, and sections Masson stained in order to assess the amount of inflammation/fibrosis.

FIG. 3:
BAL fluid from 2 mice of each experimental groups was obtained in order to measure protein (FIG. 3a) and cell content (FIGS. 3b-e). In order to collect BAL fluid, a cannula has been inserted into previously prepared trachea, after which lungs has been lavaged with 3 volumes of PBS (total volume 1 mL). Protein content has been measured and total and differential cell counts have been assessed by performing cytospin with BAL fluid, staining the cells, count and identify the different cell types based on their morphology.

FIG. 4:
A Bleomycin induced lung fibrosis model was used to test the effect of MQ22.101 and MQ22.101b/d on inflammation and fibrosis in the lung. At day 0 mice received an oropharyngeal instillation of bleomycin. On days 0, 2 and 5 bleomycin treated groups received an intraperitoneal injection containing 1 mg mouse antibody MQ22.101, 1 mg mouse antibody MQ20.101 (irrelevant isotype matched control antibody) or PBS. Two additional bleomycin treated groups received 1 mg humanized MQ22.101 (MQ22.101b/d) or 1 mg human antibody MQR2.101 (human control antibody) on days 2 and 5. MQR2.101 is a control antibody. Pirfenidone has been dosed daily from day 0 to day 13. Two weeks after bleomycin or PBS instillation, mice were euthanized with an overdose of ketamine hydrochloride (Narketan) and xylazinehydrochloride (Rompun). Lungs were weighed and fixed with 10% buffered formalin for histopathalogical analysis Madtes scoring has been performed according Tables 3 and 4. Score: 0-10.
*$p<0.05$ versus vehicle, Mann-Whitney test.

The invention claimed is:

1. A method for the treatment of a subject having idiopathic pulmonary fibrosis, the method comprising:
    obtaining an antibody specifically reactive with a citrullinated epitope on the N-terminus of deiminated histone H2A or H4; and
    administering the antibody to the subject,
    wherein the antibody comprises a heavy chain CDR1 domain comprising SEQ ID NO: 5, a heavy chain CDR2 domain comprising SEQ ID NO: 6, a heavy chain CDR3 domain comprising SEQ ID NO: 7, a light chain CDR1 domain comprising SEQ ID NO: 8, a light chain CDR2 domain comprising SEQ ID NO: 9, and a light chain CDR3 domain comprising SEQ ID NO: 10.

2. The method according to claim 1, wherein the citrullinated epitope resides on a peptide comprising SEQ ID NO: 1 or SEQ ID NO: 2.

3. The method according to claim 1, wherein the antibody is a monoclonal antibody.

4. The method according to claim 1, wherein the antibody comprises a heavy and light chain as contained in monoclonal antibody RmmAb 22.101 produced by the hybridoma cell line deposited with the DSMZ under deposit number ACC 3031.

5. The method according to claim 1, wherein the antibody competes with monoclonal antibody RmmAb 22.101 for binding to SEQ ID NO:1 or SEQ ID NO: 2.

6. A method for reducing fibrotic progression in a subject having idiopathic pulmonary fibrosis, the method comprising:
    obtaining an antibody specifically reactive with a citrullinated epitope on the N-terminus of deiminated histone H2A or H4; and
    administering the antibody to the subject,
    wherein the antibody comprises a heavy chain CDR1 domain comprising SEQ ID NO: 5, a heavy chain CDR2 domain comprising SEQ ID NO: 6, a heavy chain CDR3 domain comprising SEQ ID NO: 7, a light chain CDR1 domain comprising SEQ ID NO: 8, a light chain CDR2 domain comprising SEQ ID NO: 9, and a light chain CDR3 domain comprising SEQ ID NO: 10.

7. A method for the treatment of a subject having idiopathic pulmonary fibrosis, the method comprising:
    administering to the subject a peptide comprising the N-terminus of deiminated histone H2A or H4;
    wherein the N-terminus of the deiminated histone H2A or H4 comprises a citrullinated epitope.

* * * * *

SEQUENCE LISTING

<160> NUMBER OF SEQ ID NOS: 12

<210> SEQ ID NO 1
<211> LENGTH: 12
<212> TYPE: PRT
<213> ORGANISM: Homo sapiens
<220> FEATURE:
<221> NAME/KEY: Xaa
<222> LOCATION: (3)..(3)
<223> OTHER INFORMATION: Xaa is citrulline

<400> SEQUENCE: 1

Ser Gly Xaa Gly Lys Gln Gly Gly Lys Ala Arg Ala
1               5                   10

<210> SEQ ID NO 2
<211> LENGTH: 23
<212> TYPE: PRT
<213> ORGANISM: Homo sapiens
<220> FEATURE:
<221> NAME/KEY: Xaa
<222> LOCATION: (3)..(3)
<223> OTHER INFORMATION: Xaa is citrullin
<220> FEATURE:
<221> NAME/KEY: Xaa
<222> LOCATION: (3)..(3)
<223> OTHER INFORMATION: Xaa is citrulline

<400> SEQUENCE: 2

Ser Gly Xaa Gly Lys Gly Gly Lys Gly Leu Gly Lys Gly Gly Ala Lys
1               5                   10                  15

Arg His Arg Lys Val Leu Arg
            20

<210> SEQ ID NO 3
<211> LENGTH: 12
<212> TYPE: PRT
<213> ORGANISM: Homo sapiens

<400> SEQUENCE: 3

Ser Gly Arg Gly Lys Gln Gly Gly Lys Ala Arg Ala
1               5                   10

<210> SEQ ID NO 4
<211> LENGTH: 23
<212> TYPE: PRT
<213> ORGANISM: Homo sapiens

<400> SEQUENCE: 4

Ser Gly Arg Gly Lys Gly Gly Lys Gly Leu Gly Lys Gly Gly Ala Lys
1               5                   10                  15

Arg His Arg Lys Val Leu Arg
            20

<210> SEQ ID NO 5
<211> LENGTH: 7
<212> TYPE: PRT
<213> ORGANISM: Homo sapiens

<400> SEQUENCE: 5

Gly Tyr Thr Phe Thr Asn Tyr
1               5

<210> SEQ ID NO 6
<211> LENGTH: 8
<212> TYPE: PRT

<213> ORGANISM: Homo sapiens

<400> SEQUENCE: 6

Ile Asn Thr Tyr Ser Gly Glu Ala
1               5

<210> SEQ ID NO 7
<211> LENGTH: 15
<212> TYPE: PRT
<213> ORGANISM: Homo sapiens

<400> SEQUENCE: 7

Leu Arg Gly Tyr Thr Tyr Gln Ser Phe Asp Glu Gly Gly Asp Tyr
1               5                   10                  15

<210> SEQ ID NO 8
<211> LENGTH: 11
<212> TYPE: PRT
<213> ORGANISM: Homo sapiens

<400> SEQUENCE: 8

Gln Ser Leu Leu Asp Ser Asp Gly Lys Thr Tyr
1               5                   10

<210> SEQ ID NO 9
<211> LENGTH: 3
<212> TYPE: PRT
<213> ORGANISM: Homo sapiens

<400> SEQUENCE: 9

Leu Val Ser
1

<210> SEQ ID NO 10
<211> LENGTH: 9
<212> TYPE: PRT
<213> ORGANISM: Homo sapiens

<400> SEQUENCE: 10

Trp Gln Gly Thr His Phe Pro Tyr Thr
1               5

<210> SEQ ID NO 11
<211> LENGTH: 367
<212> TYPE: DNA
<213> ORGANISM: mus musculus

<400> SEQUENCE: 11
cggatccagt tggtgcagtc tggacctgaa ctgaagaagc ctggtgaggc agtcaagatc        60
tcctgtaagg cttctggata taccttcaca aactatggta tgcactggat gaaacagact       120
ccaggaaagg attttaggtg gatgggctgg ataaacacct acagtggaga ggcaacatat       180
gttgatgact caagggacg cttcgccttc tctttgggaa cctctgccag cactgcctat       240
ttgcagatca acaacctcaa gaatgacgac acggctacat atttctgttt aagaggctat       300
acttaccaaa gtttcgacga agggggcgac tactggggcc agggcaccgc tctcacagtc       360
tcctcag                                                                 367

<210> SEQ ID NO 12
<211> LENGTH: 338
<212> TYPE: DNA
<213> ORGANISM: mus musculus

```
<400> SEQUENCE: 12
gatgttgtga tgacccagac tccactcact ttgtcggtta ccactggaca accagcctcc      60
atctcttgca agtcaagtca gagcctcttg gatagtgatg gaaagacata tttgaattgg     120
ttgtttcaga ggccaggcca gtctccaaag cgcctaatat atctggtgtc taaactggac     180
tctggagtcc ctgacaggtt cactggcagt ggatcaggga cagatttcac actgaaaatc     240
agcagagtgg aggctgagga tttgggaatt tattattgct ggcaaggtac acattttccg     300
tacacgttcg gaggggggac caatttggaa ataaaacg                             338
```